US 9,163,988 B2

(12) United States Patent
Dogariu

(10) Patent No.: US 9,163,988 B2
(45) Date of Patent: Oct. 20, 2015

(54) DETECTION SYSTEMS AND METHODS USING COHERENT ANTI-STOKES RAMAN SPECTROSCOPY

(71) Applicant: Trustees of Princeton University, Princeton, NJ (US)

(72) Inventor: Arthur Dogariu, Hamilton, NJ (US)

(73) Assignee: Trustees of Princeton University, Princeton, NJ (US)

( * ) Notice: Subject to any disclaimer, the term of this patent is extended or adjusted under 35 U.S.C. 154(b) by 14 days.

(21) Appl. No.: 14/092,686

(22) Filed: Nov. 27, 2013

(65) Prior Publication Data

US 2014/0226157 A1     Aug. 14, 2014

Related U.S. Application Data

(60) Provisional application No. 61/730,792, filed on Nov. 28, 2012.

(51) Int. Cl.
  *G01J 3/44*     (2006.01)
  *G01N 21/65*    (2006.01)
  *G01J 3/02*     (2006.01)

(52) U.S. Cl.
  CPC ............. *G01J 3/4412* (2013.01); *G01J 3/0208* (2013.01); *G01J 3/0216* (2013.01); *G01J 3/44* (2013.01); *G01N 21/65* (2013.01); *G01N 2021/653* (2013.01)

(58) Field of Classification Search
  CPC ............... G01N 21/65; G01N 21/658; G01N 2021/656; G01J 3/02; G01J 3/44
  USPC ............................................. 356/301, 72–73
  See application file for complete search history.

(56) References Cited

U.S. PATENT DOCUMENTS

2009/0252467 A1   10/2009  Okuno
2010/0020318 A1*   1/2010  Lee et al. ...................... 356/301
2011/0128538 A1*   6/2011  Cerullo et al. ................ 356/301

FOREIGN PATENT DOCUMENTS

CN              102162907          5/2012

OTHER PUBLICATIONS

International Search Report and Written Opinion dated Feb. 26, 2014 from International Application No. PCT/US2013/072391, pp. 1-14.
Dogariu, Arthur et al. Coherent Anti-Stokes Raman Spectroscopy for detecting explosives in real-time. Chemical, Biological, Radiological, Nuclear, and Explosives (CBRNE) Sensing XIII, May 11, 2012, vol. 8358, No. 1, pp. 8358-1-8358-9.
Dogariu, Arthur et al. Photonic Crystal Fiber Based Time-Resolved Coherent Anti-Stokes Raman Scattering Spectroscopy. 2007 Conference on Lasers and Electro-Optics, May 5-11, 2007, pp. 1-2.

* cited by examiner

*Primary Examiner* — Abdullahi Nur
(74) *Attorney, Agent, or Firm* — MH2 Technology Law Group, LLP

(57)     ABSTRACT

Systems and methods for remote and/or portable detection are provided. The system can include a source of coherent laser pulses, components for converting the coherent laser pulses into first beam pulses at a first wavelength value, second beam pulses at a second wavelength value, and third beam pulses at a third wavelength value. Systems can further include optical components configured to delay at least one of the first beam pulses, the second beam pulses, and the third beam pulses in order to create delayed beam pulses, and a focusing component configured direct a substantially collinear combination of the delayed beam pulses and two of a set of: the first beam pulses, the second beam pulses, and the third beam pulses, onto a sample.

28 Claims, 11 Drawing Sheets

DETECTION SYSTEMS AND METHODS USING COHERENT ANTI-STOKES RAMAN SPECTROSCOPY

PRIORITY

This application claims the benefit of priority from U.S. Provisional Application No. 61/730,792, filed Nov. 28, 2012, which is herein incorporated by reference in its entirety.

STATEMENT REGARDING FEDERALLY SPONSORED RESEARCH OR DEVELOPMENT

Aspects of this invention were made with U.S. Government support under Prime Awards #HSHQDC-10-C-00100 and #HSHQDC-09-C-00135 awarded by the U.S. Department of Homeland Security. The U.S. Government has certain rights in the invention.

FIELD

This disclosure relates to detection systems and methods using coherent anti-stokes Raman spectroscopy.

BACKGROUND

Vibrational spectroscopy can be a powerful tool for chemical composition analysis. The interaction of light and matter can allow the interrogation and identification of vibrational states that are unique to each molecular structure. In this regard, Raman vibrational spectroscopy can provide exceptional molecular identification. Based on inelastic scattering of photons off molecular vibrations, the Raman effect can be very well suited for chemical recognition.

FIGS. 1 and 2 depict energy diagrams that illustrate a conventional Raman scattering process. If a probe beam with energy 155 is incident on a sample with ground state 100 (designated as |c>), available excited vibrational mode 110 (designated as |b>), and available energy level 150 (designated as |a>) as depicted in FIGS. 1 and 2, then the sample can generate a spontaneous Raman spectrum—one associated transition of which is depicted with energy 135, and which corresponds to a "Stokes shift" in the energy 155 of the probe beam. Note that a virtual state 130 (between excited vibrational mode 110 and energy level 150) is identified as bridging the transition between the probe beam of energy 155 and the emitted radiation associated with the Stokes shift at energy 135. The excited vibrational mode correlated with the Stokes shift is a vibrational mode that is randomly excited (a difference between levels |b>, and |c>). Furthermore, although excited vibrational mode 110 is identified in FIGS. 1 and 2 with a single label |b>, there can be many vibrational modes that are available and that differ in energy (which is indicated by the double line in FIGS. 1 and 2).

A disadvantage of conventional Raman spectroscopy, which relies upon incoherent scattering, is the low probability of this process. For example, a low conversion efficiency of pump photons into Stokes shifted photons can make spontaneous Raman measurements sometimes lengthy and undesirable for fast identification of molecular vibrations. Where applied to the nondestructive detection of trace explosives from large distance in the presence of interferants, it can be difficult to use conventional Raman spectroscopy in a rapid and reliable manner.

SUMMARY

In one aspect, the present disclosure is directed to a system for remote detection. The system can include a source of coherent laser pulses, a parametric amplifier configured to convert the coherent laser pulses into first beam pulses at a first wavelength value and second beam pulses at a second wavelength value different from the first wavelength value, and a first optical component configured to select third beam pulses from the coherent laser pulses at a third wavelength value different from the second wavelength value and the first wavelength value. The system can further include a second optical component configured to delay at least one of the first beam pulses, the second beam pulses, and the third beam pulses in order to create delayed beam pulses, and a focusing component configured direct a substantially collinear combination of the delayed beam pulses and two of a set of: the first beam pulses, the second beam pulses, and the third beam pulses, onto a line, the line being substantially perpendicular to a direction of propagation of the collinear combination.

In another aspect, the disclosure is directed to a method for remote detection. The method can include providing a source of coherent laser pulses, converting the coherent laser pulses into first beam pulses at a first wavelength value and second beam pulses at a second wavelength value different from the first wavelength value, and selecting third beam pulses from the coherent laser pulses at a third wavelength value different from the second wavelength value and the first wavelength value. The method can further include delaying at least one of the first beam pulses, the second beam pulses, and the third beam pulses in order to create delayed beam pulses, and directing a substantially collinear combination of the delayed beam pulses and two of the set of: the first beam pulses, the second beam pulses, and the third beam pulses, onto a line, the line being substantially perpendicular to a direction of propagation of the collinear combination.

In a further aspect, the disclosure is directed to a portable detection system. The portable detection system can include a source of coherent laser pulses, where the source is configured to provide the laser pulses at a plurality of power values, and where the coherent laser pulses are configured to exhibit a first spectral distribution as a function of the plurality of power values. The system can also include a length of photonic crystal fiber configured to generate coherent, converted pulses from the coherent laser pulses, where the coherent, converted pulses exhibit a second spectral distribution as a function of the plurality of power values, wherein the second spectral distribution is different from the first spectral distribution at at least one power value of the plurality of power values. The system can further include a first optical system configured to select first beam pulses at a first wavelength value and second beam pulses at a second wavelength value different from the first wavelength value from the coherent, converted pulses, and can include a second optical system configured to select third beam pulses from the coherent, converted pulses at a third wavelength value different from the second wavelength value and the first wavelength value. The system can also include a third optical component configured to delay at least one of the first beam pulses, the second beam pulses, and the third beam pulses in order to create delayed beam pulses.

In yet an additional aspect, the present disclosure is directed to a method for portable detection. The method can include providing a source of coherent laser pulses, where the source is configured to provide the laser pulses at a plurality of power values, and where the coherent laser pulses are configured to exhibit a first spectral distribution as a function of the plurality of power values. The method can also include providing a length of photonic crystal fiber configured to generate coherent, converted pulses from the coherent laser pulses, where the coherent, converted pulses exhibit a second spectral distribution as a function of the plurality of power values, wherein the second spectral distribution is different from the first spectral distribution at at least one power value of the plurality of power values, selecting first beam pulses at a first wavelength value and second beam pulses at a second wavelength value different from the first wavelength value from the coherent, converted pulses; selecting third beam pulses from the coherent, converted pulses at a third wavelength value different from the second wavelength value and the first wavelength value. Further still, the method can include delaying at least one of the first beam pulses, the second beam pulses, and the third beam pulses in order to create delayed beam pulses; and directing a substantially collinear combination of the delayed beam pulses and two of the set of: the first beam pulses, the second beam pulses, and the third beam pulses onto a sample.

Additional features and advantages will be set forth in part in the description which follows, being apparent from the description of or learned by practice of the disclosed embodiments. The features and advantages will be realized and attained by means of the elements and combinations particularly pointed out in the appended claims.

It is to be understood that both the foregoing general description and the following detailed description are exemplary and explanatory only and are not restrictive of the scope of the embodiments, as claimed.

BRIEF DESCRIPTION OF THE DRAWINGS

The accompanying drawings, which are incorporated in and constitute a part of this specification, illustrate embodiments and, together with the description, serve to explain the features, advantages, and principles of the disclosed embodiments.

DETAILED DESCRIPTION

Reference will now be made in detail to the one or more embodiments, characteristics of which are illustrated in the accompanying drawings. Wherever possible, the same reference numbers will be used throughout the drawings to refer to the same or like parts.

Consistent with the current disclosure, a coherent Raman process can exhibit higher conversion efficiencies over a conventional Raman process, which can improve the speed with which measurements are acquired. Accordingly, Coherent Anti-Stokes Raman Scattering (CARS) can be a powerful spectroscopic technique for probing Raman active resonances in gases, liquids, and solids. In CARS, one coherently excites the vibrational levels using two beams, a pump beam and a Stokes shifted beam, which greatly enhances the probability of Raman scattering for a probe beam.

Figure 1:
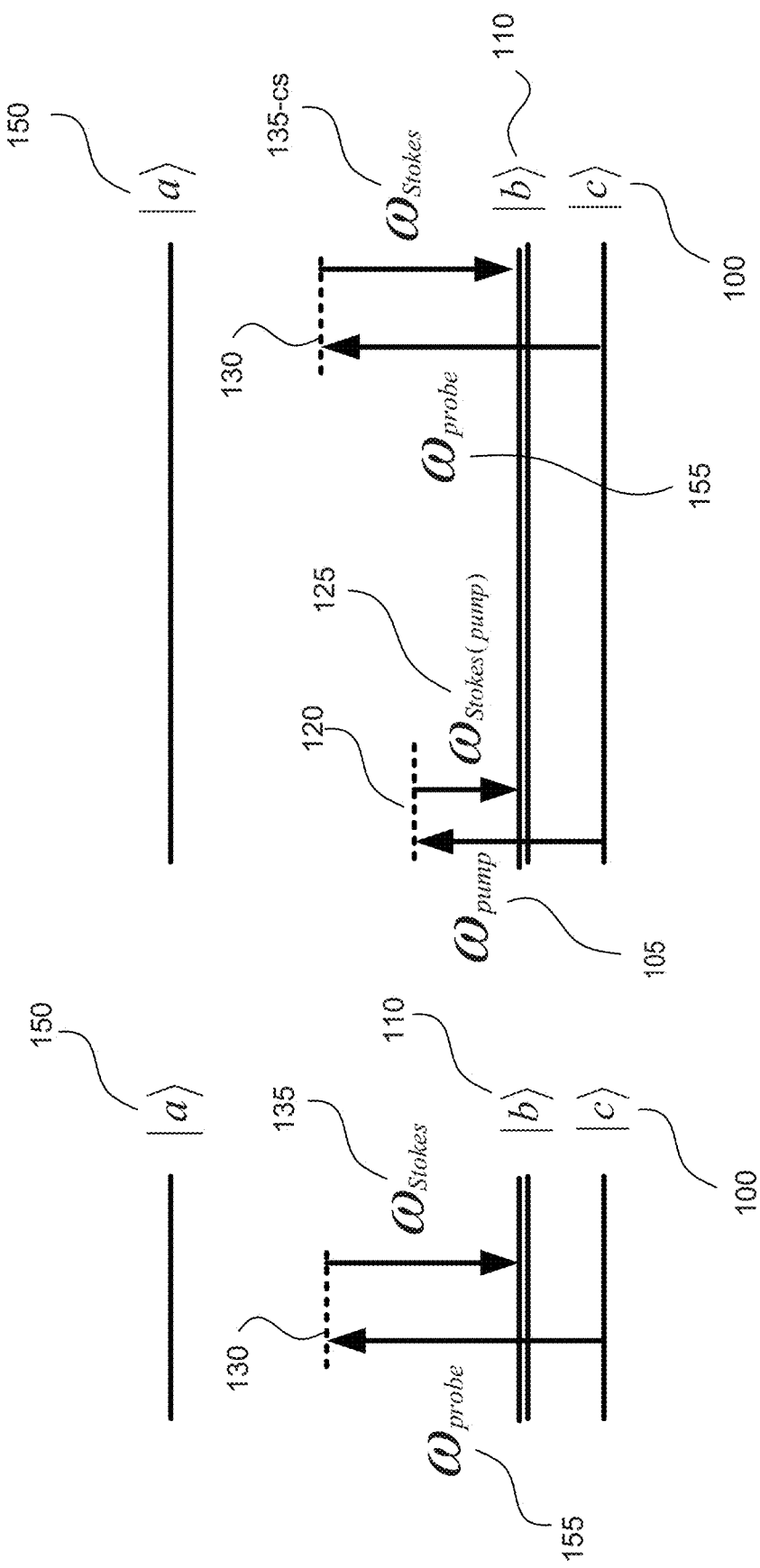
FIG. 1 depicts energy level diagrams illustrating a conventional Raman process, and a corresponding coherent Raman-process.

Returning to FIGS. 1 and 2, FIG. 1 also depicts an energy diagram that illustrates a coherent Raman scattering process. As before, the probe beam with energy 155 can be incident on the sample with ground state 100 (designated as |c>), available vibrational mode 110 (designated as |b>), and available energy level 150 (designated as |a>) as depicted in FIG. 1. In addition to the probe beam, however, a pump beam with energy 105 and a Stokes-shifted pump beam with energy 125 can be used to coherently excite the vibrational mode 110. In FIG. 1, a virtual level 120 is illustrated as bridging a transition between the pump beam of energy 105 and the Stokes-shifted pump beam of energy 125. Because the Stokes-shifted available vibrational mode 110 (designated as |b>) is excited as a result of the action of the pump beam and the Stokes-shifted pump beam, the conventional Raman scattering process includes a coherent contribution to the Stokes spectrum of the probe beam—designated in FIG. 1 with a the label 135-cs. Consequently, if one sends the pump beam with energy 105 and a Stokes-shifted pump beam with energy 125 just before sending the probe beam at energy 155, one can detect a Coherent Stokes Raman Scattering (CSRS) signal to level |b> when probing level |c>.

Figure 2:
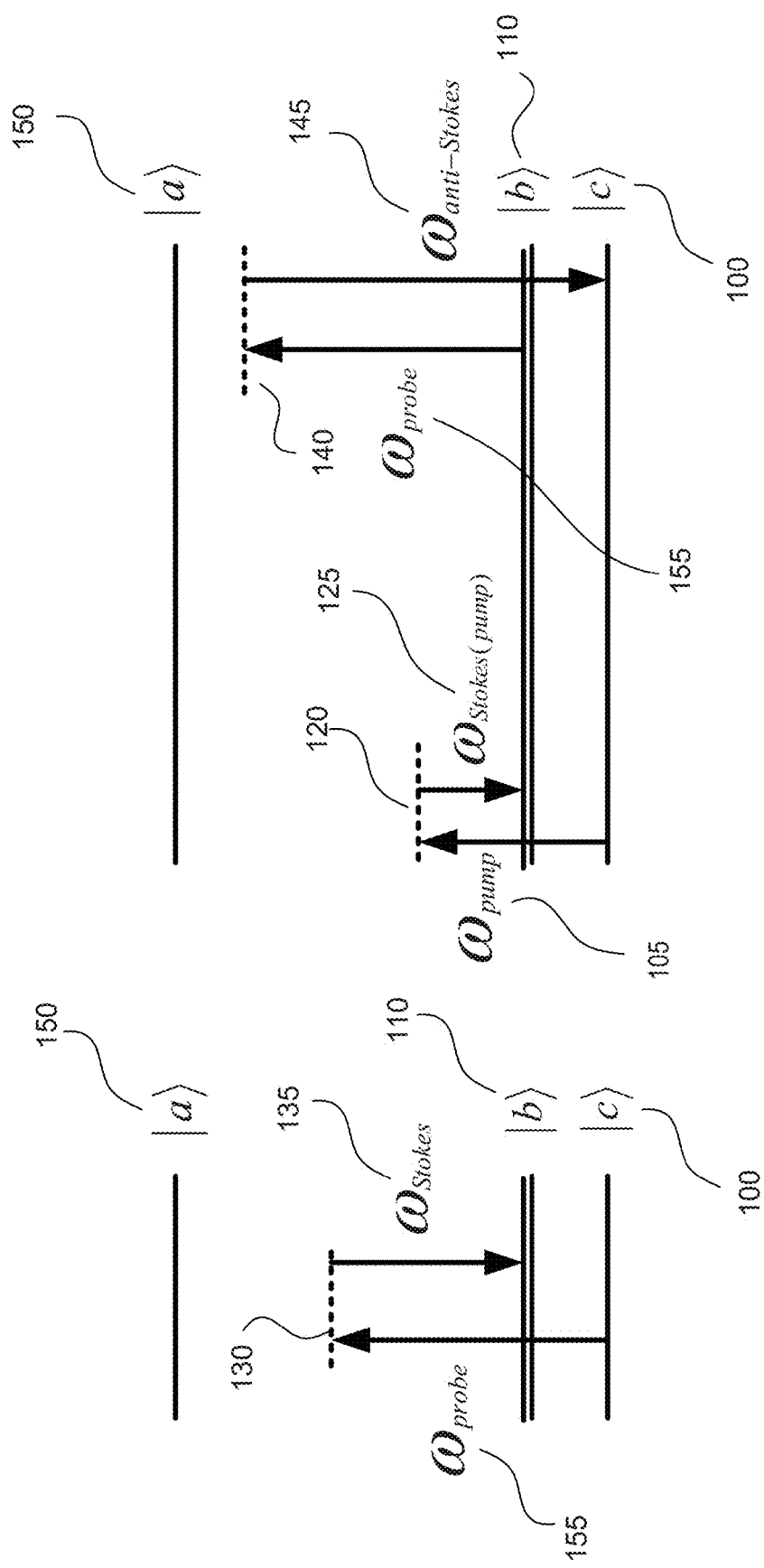
FIG. 2 depicts energy level diagrams illustrating the conventional Raman process of FIG. 1 and a corresponding coherent anti-stokes Raman-process.

Similarly, FIG. 2 depicts an energy diagram that illustrates a coherent Anti-Stokes Raman scattering process. Again, the probe beam with energy 155 can be incident on the sample with ground state 100 (designated as |c>), available vibrational mode 110 (designated as |b>), and available energy level 150 (designated as |a>) as depicted in FIG. 2. As in FIG. 1, the pump beam with energy 105 and a Stokes-shifted pump beam with energy 125 can be used to coherently excite the vibrational mode 110. Moreover, in FIG. 2—as in FIG. 1—a virtual energy level 120 is illustrated as bridging a transition between the pump beam of energy 105 and the Stokes-shifted pump beam of energy 125. In this scenario, however, because the Stokes-shifted vibrational mode 110 (designated as |b>) is excited as a result of the action of the pump beam and the Stokes-shifted pump beam, the conventional Raman scattering process includes a further coherent contribution to the spectrum of the probe beam—designated in FIG. 2 with a the label 145 and corresponding to a transition from the vibrational mode designated as |b> to a further virtual level 140 (which exhibits an energy difference from the excited vibrational mode 110 by the probe energy 155). As depicted in FIG. 2, the virtual level 140 transitions back to the ground state 100—designated as |c>. Accordingly, consistent with the process depicted in FIG. 2, if one sends the pump beam with energy 105 and a Stokes-shifted pump beam with energy 125 just before sending the probe beam at energy 155, one can detect a Coherent Anti-Stokes Raman Scattering (CARS) signal to ground state |c> when probing excited vibrational mode |b>.

Where a conventional Stokes-shifted spectrum is red-shifted in energy relative to a probe beam, a spectrum associated with the CARS transition depicted in FIG. 2 will be blue-shifted in energy relative to the probe beam.

Issues associated with analyzing a CARS spectrum can include isolating background noise contributions as a result of non-resonant four-wave mixing either from solvents, substrates, or molecules themselves. One of ordinary skill in the art would appreciate, however, that there are several ways of isolating such background noise effects in CARS measurement. For example, one can use polarization sensitive, interferometric, heterodyne, or time-resolved techniques. All these techniques can be used to increase the ratio between the resonant CARS signal and the non-resonant background noise.

Moreover, consistent with the current disclosure, time-resolved CARS can be useful because it not only proves to be a very sensitive technique for investigating molecular vibrations, but it also has the advantage of measuring another parameter: decoherence time, or the lifetime of the coherent molecular vibrations.

Figure 3:
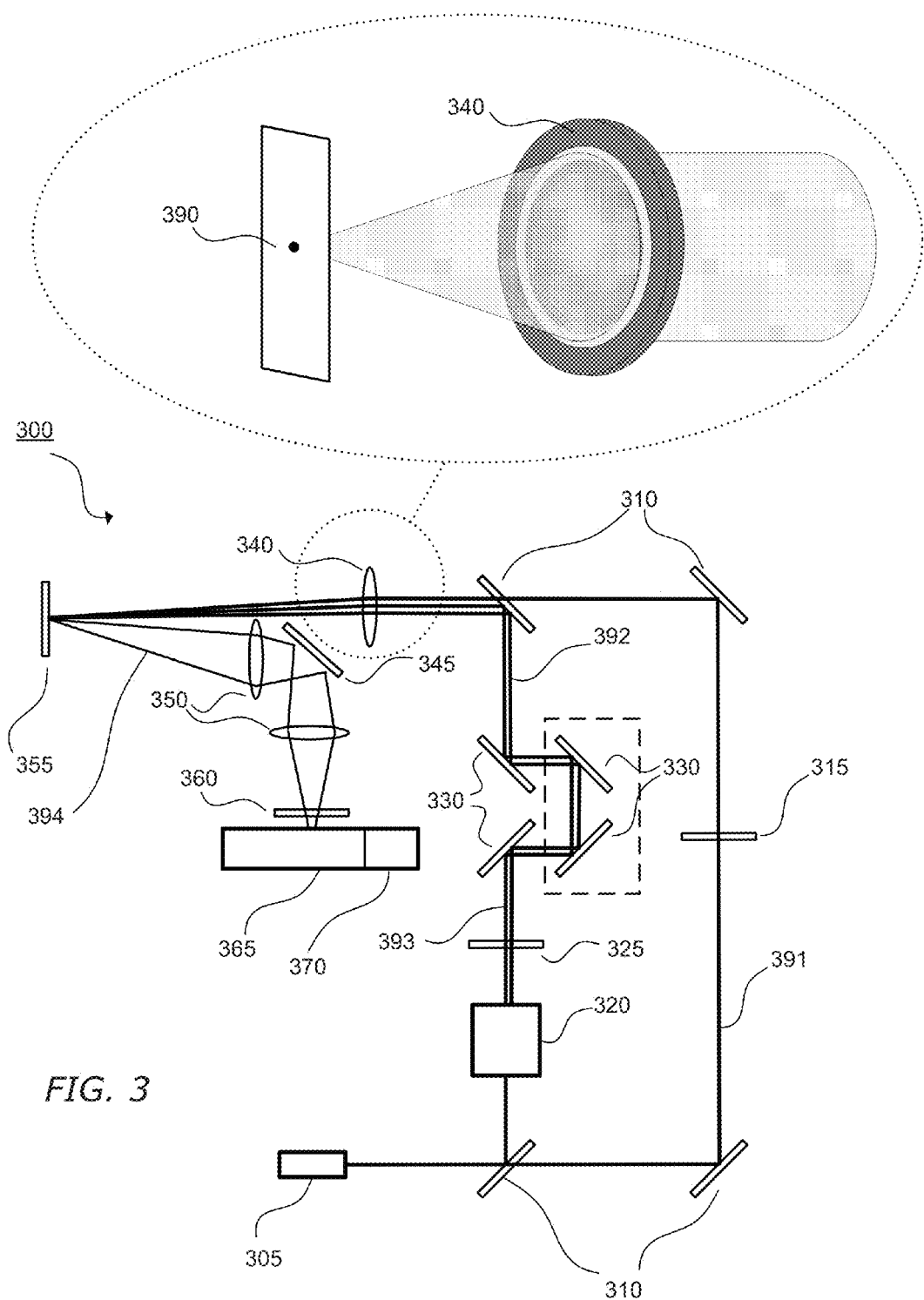
FIG. 3 depicts a system for directing three collinear beams to a point-configured target and acquiring a backscattered radiation signal.

FIG. 3 depicts a system 300 for performing time-resolved broadband CARS measurements. The system 300 includes two broadband beams (a pump beam 392 and Stokes beam 393) to excite vibrational levels of the sample, and a picosecond probe beam 391. The probe beam 391 is configured to be time-delayed from the pump beam 392 and the Stokes beam 393 so as to reduce the non-resonant signal, but not too much time-delayed so as to lose coherence between the ground state levels excited by the pump beam 392 and the Stokes beams 393. All of the beams depicted herein (including beams 391, 292, and 393 in FIGS. 3 and 4) are collinear and thereby substantially overlap, but are depicted as separate lines in FIGS. 3 and 4 only for convenience.

System 300 includes laser system 305 and parametric amplifier 320 to produce the probe beam 391, the pump beam 392, and the Stokes beam 393. In an embodiment, laser system 305 can be a femtosecond laser system. In an embodiment, system 300 can include optical parametric amplifier 320 ("OPA 320"), which can be configured to generate the pump beam 392 and the Stokes beam 393 in 100 fs pulses at wavelengths of 1.4 microns and 1.8 microns respectively. Furthermore, in an embodiment, a maximum total energy of the generated pulses in the pump beam 392 and the Stokes beam 393 can be 10 µJ. In an embodiment, the total energy of the generated pulses in the pump beam 392 and the Stokes beam 393 can also be less than approximately 1 µJ to 2 µJ. Preferably, the wavelengths of the pump beam 392, the Stokes beam 393, and the probe beam 391 lie in the near- to mid-infrared.

In a preferred embodiment, the probe beam 392 is obtained by passing a portion of the laser beam generated by the laser system 305 through a filter 315—which can be a 1 nm bandpass interference filter. One of skill in the art should appreciate that, where there is a relatively long lifetime of a vibrational coherence (such as can be associated with trace amounts of certain explosives), a few picoseconds delay can allow for recording a CARS spectra without non-resonant background. As depicted in FIG. 3, all three beams can be sent through a lens 340, which can have a focal length ranging from 20 cm to 5 meters in a preferred embodiment, and can extend up to as much as 10 m. Lens 340 can focus the three beams onto a target sample 355 with a point-configured target 390, and collecting lens 350 can provide the CARS signal to a detection system, which can be composed of a spectrometer 365 and an associated CCD camera 370. The pump beam 392 and the Stokes beam 393 can be configured to exhibit sufficient bandwidth to cover a fingerprint region between approximately 500 to 2000 cm$^{-1}$, such that system 300 can be successfully used to record the vibrational spectra of various explosives.

Consistent with this disclosure, a time-delayed CARS system, such as system 300, can measure vibrational mode lifetimes, and hence distinguish between molecules with different decoherence times. Furthermore, by tuning the pulses generated in the pump beam 392 and the Stokes beam 393, one can excite specific modes of interest, which again can help to distinguish between the spectra of different molecules. These advantages make system 300 suitable for real-time monitoring with high selectivity. For example, a vibrational spectrum that can take minutes to acquire using conventional Raman spectroscopy can be obtained in milliseconds using system 300.

Further still, it has been found that issues associated with phase-matching required for a strong coherent signal are not problematic in system 300, where the target sample 355 corresponds to a solid surface, and where the probe beam 391, the pump beam 392, and the Stokes beam 393 are collinear, and a CARS signal (associated with beam 394) is recorded in the backscattered configuration.

Real-time detection can require the use of fast and reliable raw signal processing and pattern recognition that operates in an automated way. For example, and without limitation, the following processing steps can be implemented for operation in near-real time, considering time windows for each spectrum acquisition than can range from tens to hundreds of milliseconds: (1) using un-decimated discrete wavelet transform for de-noising; (2) baseline correction of the de-noised spectrum performed by polynomial fitting; and (3) detecting local maxima (peaks) in each de-noised, baseline-corrected and normalized spectrum.

In connection with using un-decimated discrete wavelet transform for de-noising, hard thresholding of the wavelet coefficients can be based on the median absolute deviation of the raw signal. Such hard thresholding can be a computationally efficient method for noise removal, providing a transformed signal consisting of peaks and baseline.

Moreover, in connection with detecting local maxima (peaks) in each de-noised, baseline-corrected and normalized spectrum, pre-defined parameters (e.g., without limitation, the peak width) can be obtained from the analysis of spectral signatures of the searched explosives. Further still, a real-time adjusting of the peak detection criteria can be implemented.

Consistent with this disclosure, spectral calibration of the system 300 can be performed during system initialization using a standard mercury-argon lamp. The output of the signal processing stage can consist of a de-noised, baseline-corrected and normalized spectra, along with the extracted features, such as peak positions.

A template matching algorithm can also be used for spectral signature identification, based on measuring the similarity between the current acquired and processed spectrum (S), and each of the spectral signatures (T) of the spectral library. A similarity index can be introduced that accounts for both global (shape) and local (peaks) features. In this context, similarity can be judged by the presence of common overall spectrum shape as well as common peaks.

Integration of global and local information can also be obtained by first computing similarity measures for each feature type. In this regard, waveform matching can be quantified using a normalized cross-correlation given by:

$$CCF(S, T) = \frac{\text{cov}(S, T)}{\sqrt{\text{var}(S) \cdot \text{var}(T)}}$$

A similarity measure for feature matching can be determined using Tversky's set-theoretic similarity model expressed as a combination of common and distinctive features and given by:

$$\text{Similarity}(S, T) = \frac{P_S \cap P_T}{(P_S \setminus P_T) + (P_S \setminus P_T) + P_S \cap P_T}$$

where $P_S$ and $P_T$ represents the local feature sets of the sample and template, respectively. The final score (a composite similarity index) can be determined by combining the two similarity metrics using the product rule. Explosive identification can then be formulated as a binary classification problem requiring selecting a suitable threshold.

Figure 4:
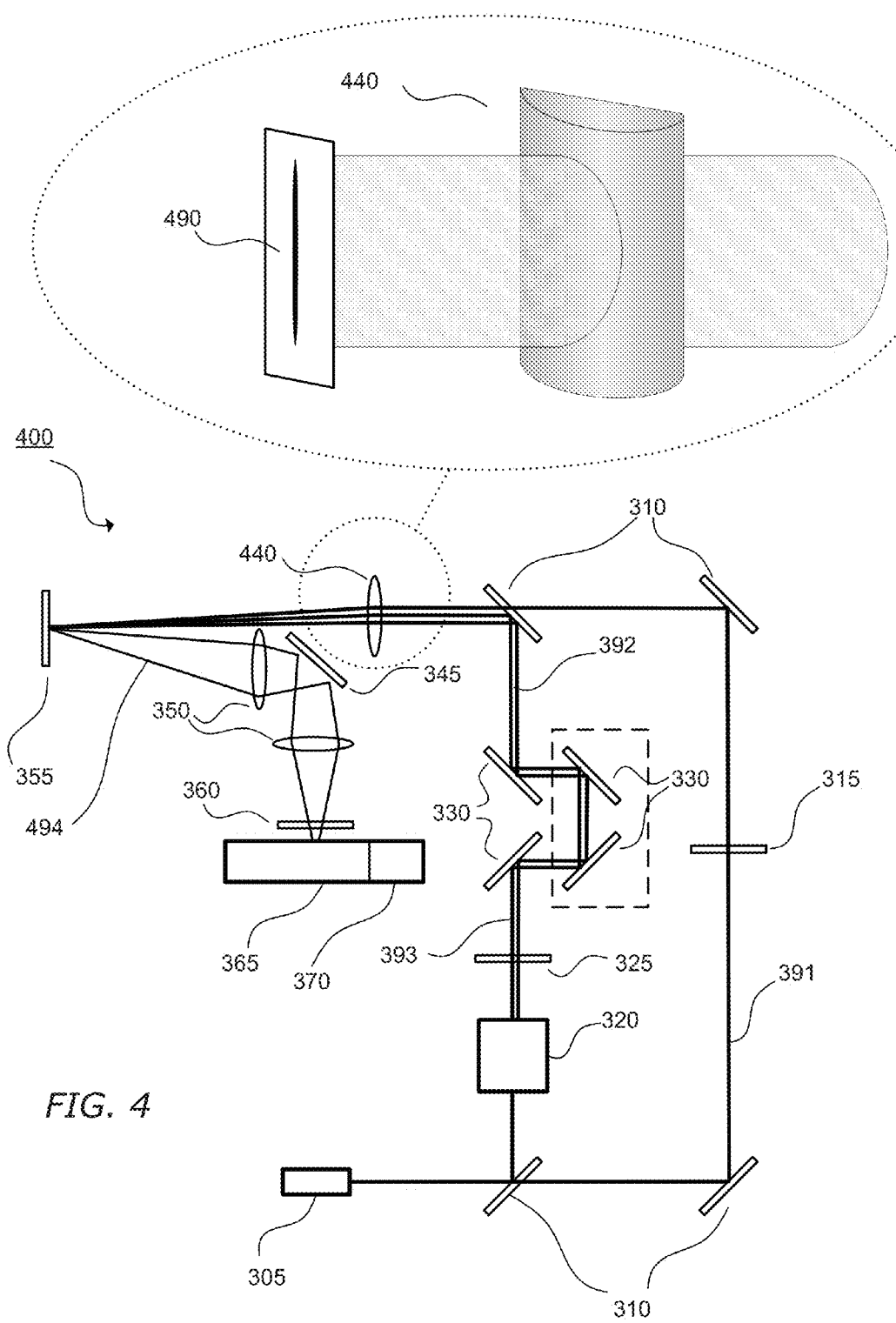
FIG. 4 depicts a system consistent with the current disclosure for directing three collinear beams to a line-configured target and acquiring a backscattered radiation signal.

Consistent with the current disclosure, FIG. 4 depicts system 400, which is configured to remotely measure spectra from a line 490. System 400 includes many of the elements of system 300—and replaces spherical lens 340 with cylindrical lens 440 in order to generate line-configured target 490. In a preferred embodiment, and without limitation, a standoff distance that can be utilized with the system 400 can preferably be up to 1 meter, and can be larger (for example, up to 5 meters) where the pulses are more energetic.

In order to record the CARS spectra (associated with beam 494) from all the points along the line-configured target 490 at the same time, system 400 is configured to image the line-configured target 490 onto the CCD camera 370 attached to the spectrometer 365 in such a way that both the spectrum and the position of the CARS emission along the line 490 are recorded.

Figure 5:
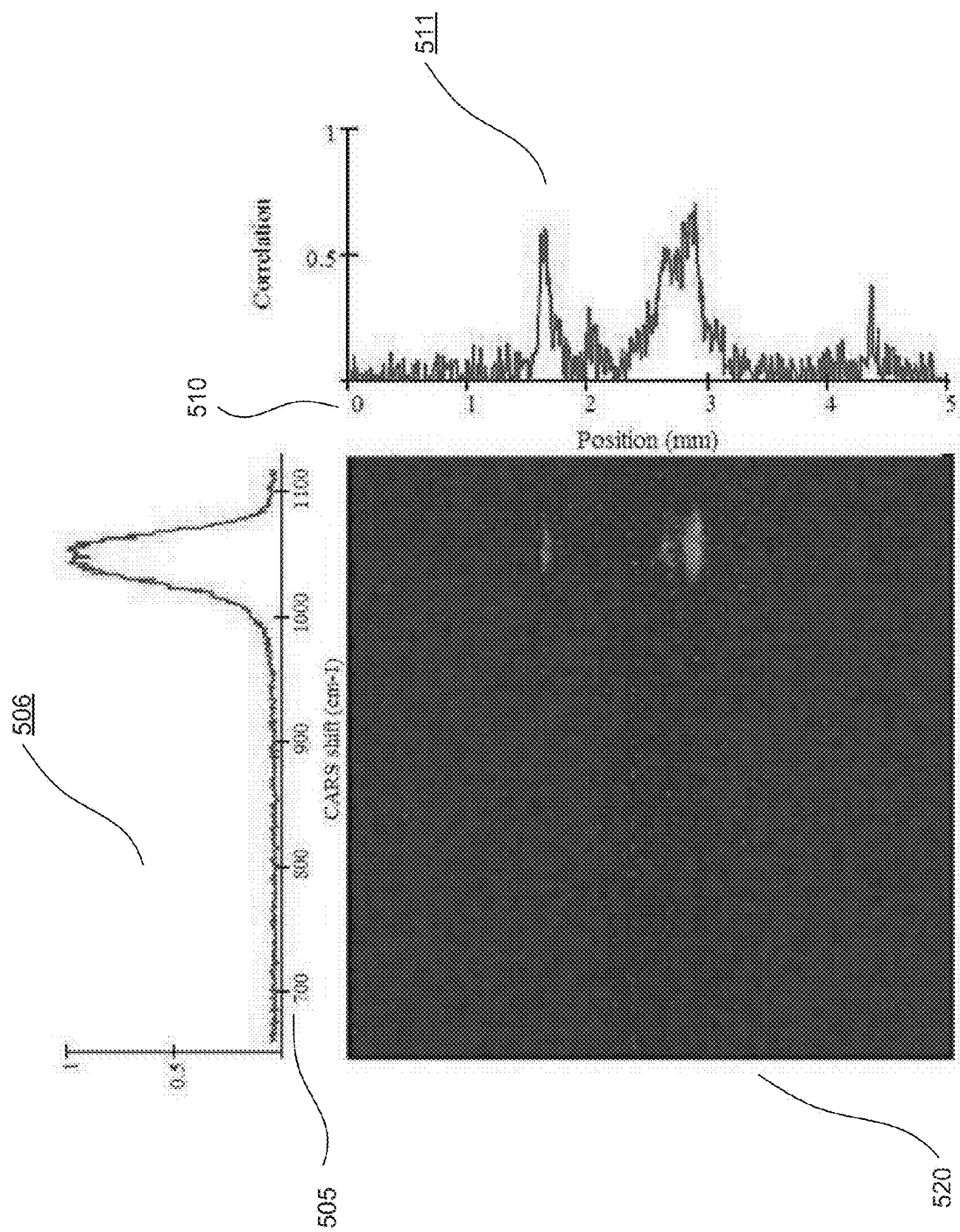
FIG. 5 depicts a back-scattered CARS spectra from the system of FIG. 4, and obtained in 100 ms from solid nitrate coated on silica.

FIG. 5 depicts a CCD image 520 obtained using system 400. The CCD image 520 is associated with the line-configured target 490 with the dimensions 5 mm×30 microns, where the three collinear beams (that is, beams 391, 392, and 393) are focused onto a sample containing trace amounts of potassium nitrate sprinkled on paper.

The CCD image 520 is configured such that a wavelength (CARS shift) is associated with an X-axis 505, while on a Y-axis 510, the 1-D sample (line) is imaged directly onto the CCD camera 370. In a preferred embodiment, the top spectrum 506 can be used to identify the tested explosive (nitrate) via a simple Pearson cross-correlation coefficient. The right side graph 511 depicts a correlation coefficient as function of the position, indicating also the amount of explosive in each point along the vertical line. The line images can be recorded in 100 ms, giving a real-time 2D hyper-spectral image of the sample with one dimension as spatial and the other as spectral. In a preferred embodiment, in order to obtain a two-dimensional image, system 400 can be configured to scan the line 490 in one dimension. Such a configuration can reduce the amount of time required for a full image, usually obtained from 2D raster-scanning a point-focused laser beam.

Figure 6:
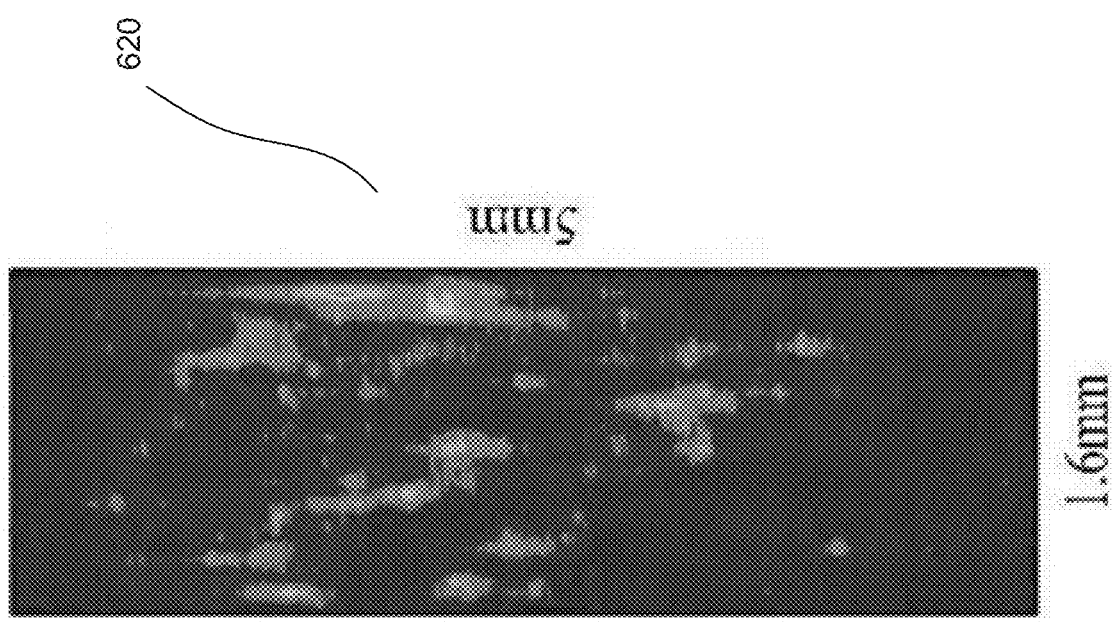
FIG. 6 depicts a 2-D hyper-spectral image from the system of FIG. 4, obtained by scanning a line-configured target of nitrate sprinkled on paper.

Image 620, depicted in FIG. 6, can be obtained from system 400 by scanning a line-configured target (such as the 5 mm line associated with the image of FIG. 5) horizontally along the sample, thereby obtaining a 2-D image of the sample tested. In a preferred embodiment, one can calculate a correlation for each line-configured target imaged on the spectrometer 365. This way, each pixel in the image can represent the correlation with the explosive (such as, without limitation, nitrate sprinkled on paper).

Figure 7:
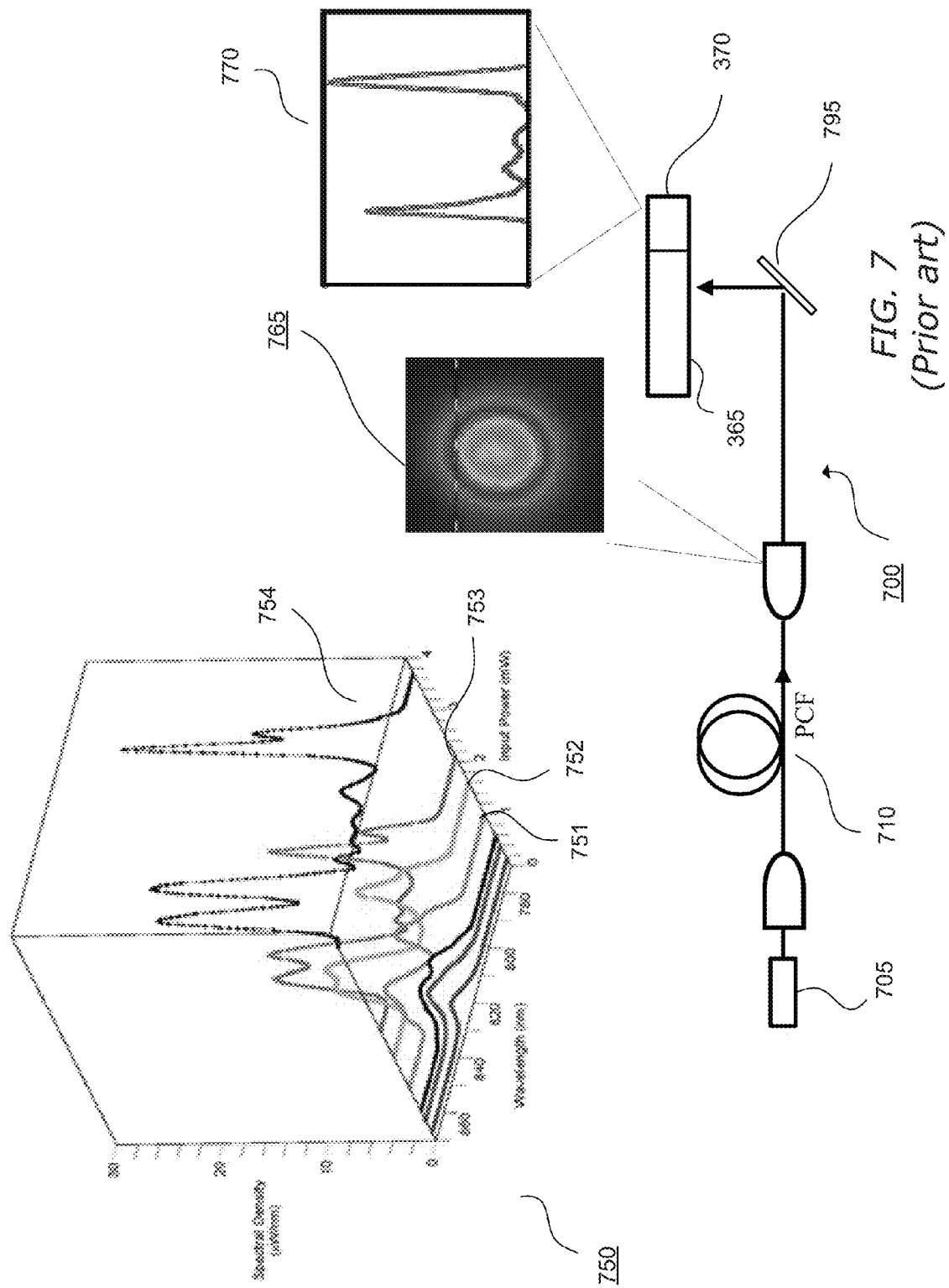
FIG. 7 depicts four-wave mixing in a photonic crystal fiber.

FIG. 7 depicts the production of Stokes and anti-Stokes coherent, collinear laser beams on either side of a fundamental beam using four-wave mixing in a photonic crystal fiber 710 ("PCF 710"). As depicted in FIG. 7, by way of example only, and consistent with this disclosure, a laser system 705 can generate an 820 nm laser beam over a range of power values. As depicted in FIG. 7, (and shown in spectral density plot 750) the power values of the laser system 705 can range from approximately 0.2 mW to approximately 4.0 mW. In an embodiment consistent with this disclosure, however, the power values of the laser system 705 will depend upon properties of the PCF 710 that is used. When the 820 nm beam passes through the PCF 710, the incident beam at an approximate initial wavelength value can be converted to collinear beams with wavelength values that are approximately centered at values greater than and less than the initial wavelength value.

As depicted in spectral density plot 750, the conversion of the initial pump beam from laser system 705 (where the pump beam has an initial wavelength value centered at approximately 820 nm) to collinear beams with wavelength values above and below the initial wavelength value of the pump beam (such as wavelength values centered at approximately 860 nm and 780 nm) occurs as a function of input power. For example, curve 751 depicts the effects of conversion of PCF 710 on an 820 nm input beam with an input power of approximately 1 mW, curve 752 depicts the effects of conversion of PCF 710 on an 832 nm input beam with an input power of approximately 1.8 mW, curve 753 depicts the effects of conversion of PCF 710 on an 820 nm input beam with an input power of approximately 2.0 mW, and curve 754 depicts the effects of conversion of PCF 710 on an 820 nm input beam with an input power of approximately 4.0 mW Also, as depicted in FIG. 7, image 765 depicts the Gaussian profile of the beams output from PCF 710.

In addition, as depicted in FIG. 7, graph 770 depicts the spectrum of the collinear beams. In a preferred embodiment, laser system 705 corresponds to a Ti:Sapphire oscillator, and corresponds to only a few tens of picoJoules/pulse.

Using the PCF 710 with laser system 705 as a source can allow one to replace laser system 305 and OPA 320, with a smaller and simpler system containing a single oscillator (which in a preferred embodiment can be fiber-based) and a small piece of photonic crystal fiber. For example, in a 15 cm length of photonic crystal fiber, one can observe the conversion of an incident probe beam (in the visible spectrum) by simply noting a color change as light propagates through the fiber.

Figure 8:
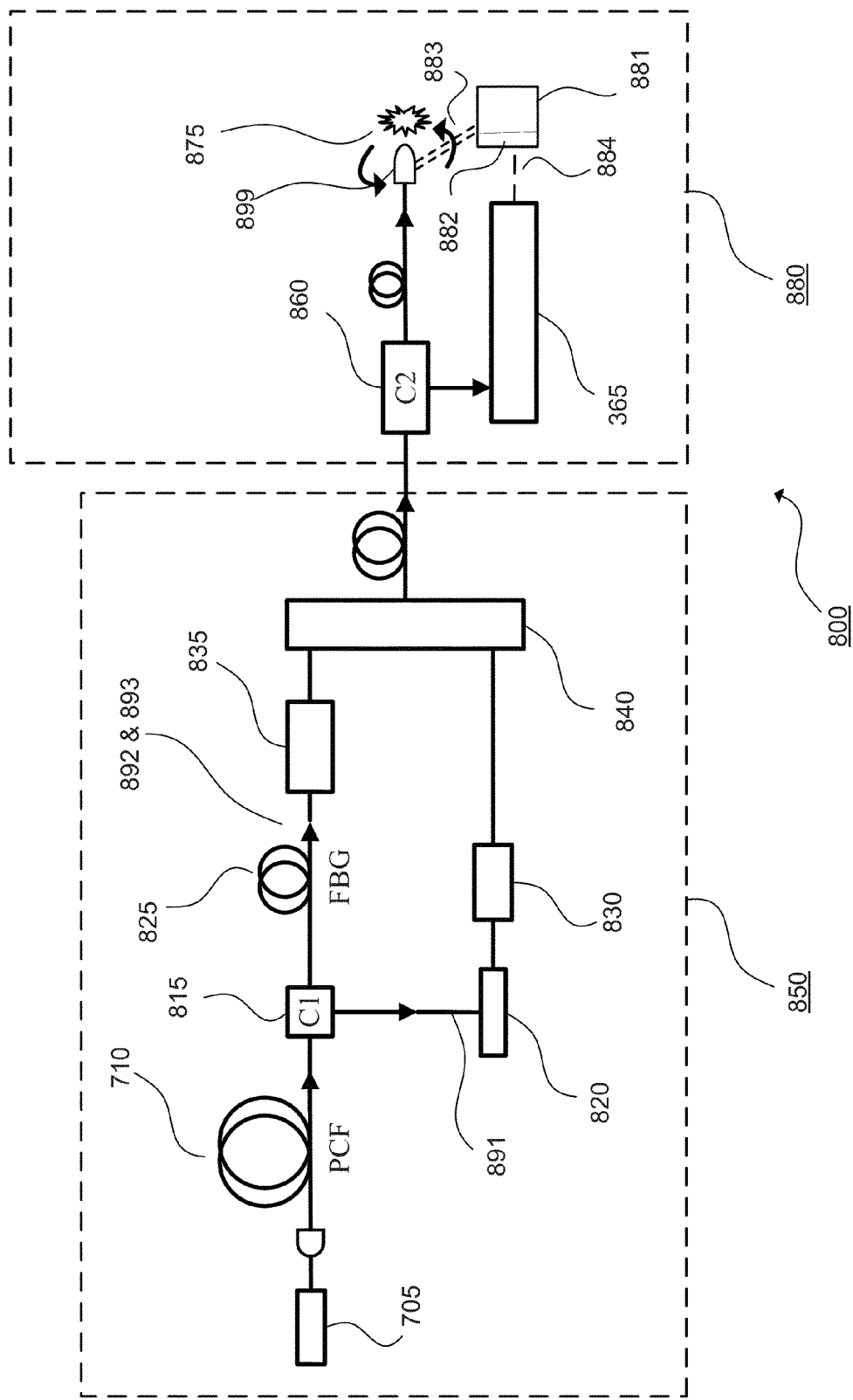
FIG. 8 depicts a system consistent with the current disclosure with an optical-fiber source for a three-color beam, and with an optical-fiber sensor.

FIG. 8 depicts system 800 consistent with the current disclosure including PCF 710 for generating a plurality of colors using four-wave mixing. System 800 can include source 850 and proximity sensor 880.

As described in connection with FIG. 7, laser system 705 can be configured to provide pulses at variable power values centered at a probe beam 891 wavelength value. The output from PCF 710 can include a plurality of colors, including the probe beam 891, a pump beam 892, and a Stokes beam 893. Circulator 815 and fiber Bragg grating 825 ("FBG 825") can be configured to isolate probe beam 891 from the output of PCF 710. Further, the FBG 825 can be configured to isolate the pump beam 892 and the Stokes beam 893 from the output of PCF 710. After passing through filter 820, probe beam 891 can be configured to exhibit a delay (using device 830) relative to the pump beam 892 and the Stokes beam 893. Device 830 provides time delay on a picosecond time scale for the probe beam 891, and can be any device conventionally known in the art. Moreover, pump beam 892 and Stokes beam 893 can be configured to pass through dispersion compensator 835. A splitter/combiner 840 can then be configured to combine the probe beam 891, the pump beam 892, and the Stokes beam 893. The output of source 850 can then be configured to pass to proximity sensor 880, which can include circulator 860 and spectrometer 365.

Proximity sensor 880 can include a fiber, which can further include a flexible terminal portion 899. The flexible terminal portion 899 can be manipulated proximal to the sample 875, and can also include a lens. The manipulation of flexible terminal portion 899 can occur by hand, or it can be implemented mechanically. For example, in a further embodiment, device 881 can be configured (via arm 883, or any suitable support structure) to move the flexible terminal portion 899 proximal to the sample, and to correlate this movement (via channel 884) with readings from spectrometer 365. This correlation can be used to generate a hyperspectral image of the scanned sample 875.

Figure 11:
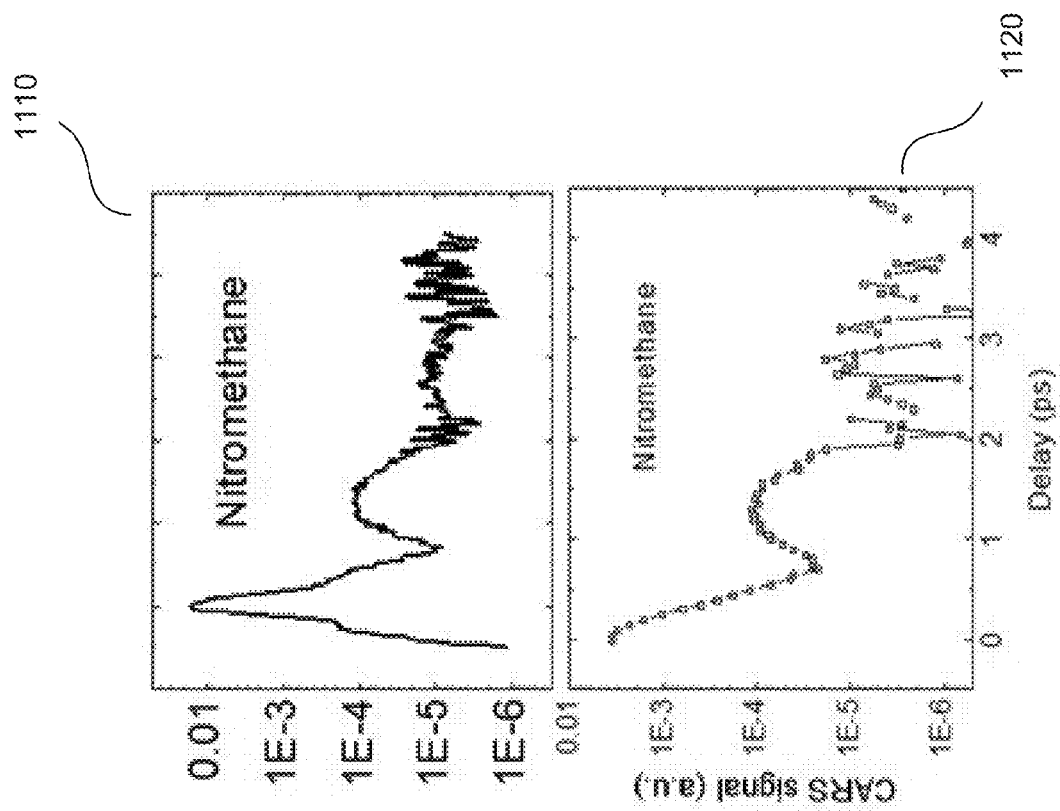
FIG. 11 depicts an exemplary result using the system of FIG. 8 compared with a result of the system of FIG. 3.

FIG. 11 depicts an exemplary result using system 800 as compared against system 300. In particular graph 1110 depicts an exemplary signal showing the detection of Nitromethane using a 1 kHz amplified system, such as can be used as system 305 and OPA 320. Graph 1120 depicts a corresponding signal showing the detection of Nitromethane using system 800.

Figure 9:
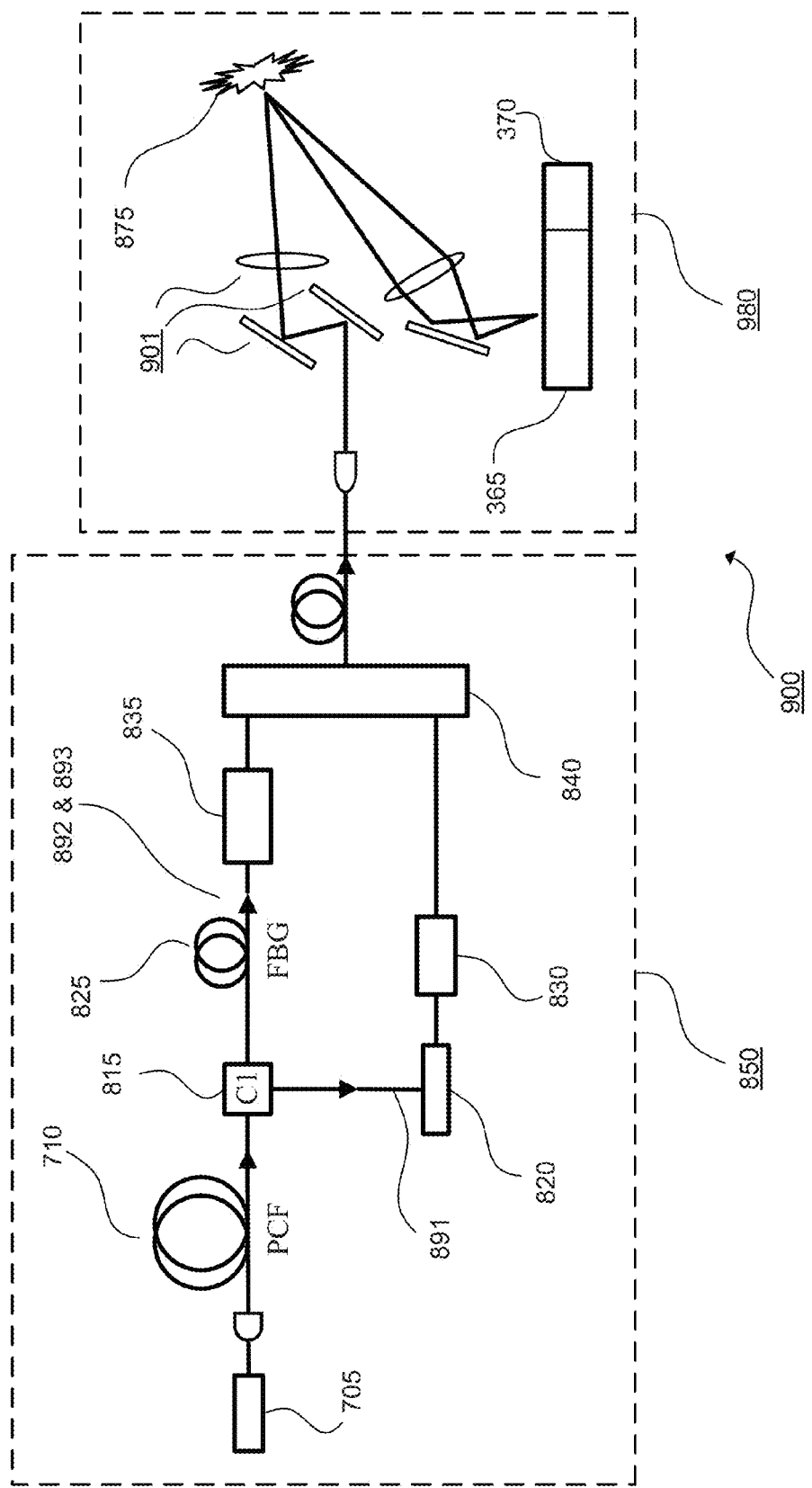
FIG. 9 depicts another system consistent with the current disclosure with an optical fiber source for a three-color beam, and utilizing an alternative imaging system.

FIG. 9 depicts system 900 consistent with the current disclosure including PCF 710 for generating a plurality of colors using four-wave mixing. System 900 can include the source 850, and can be configured for free-space imaging using system 980.

As depicted in FIG. 9, system 980 can include scanning system 901. Scanning system 901 can include any suitable combination of lens, mirrors and motorized components for raster scanning over the sample 875. As depicted in FIG. 9, the output of source 850 can then be scanned over the sample 875, with a backscattered signal acquired imaging spectrometer 365 and CCD 370.

Figure 10:
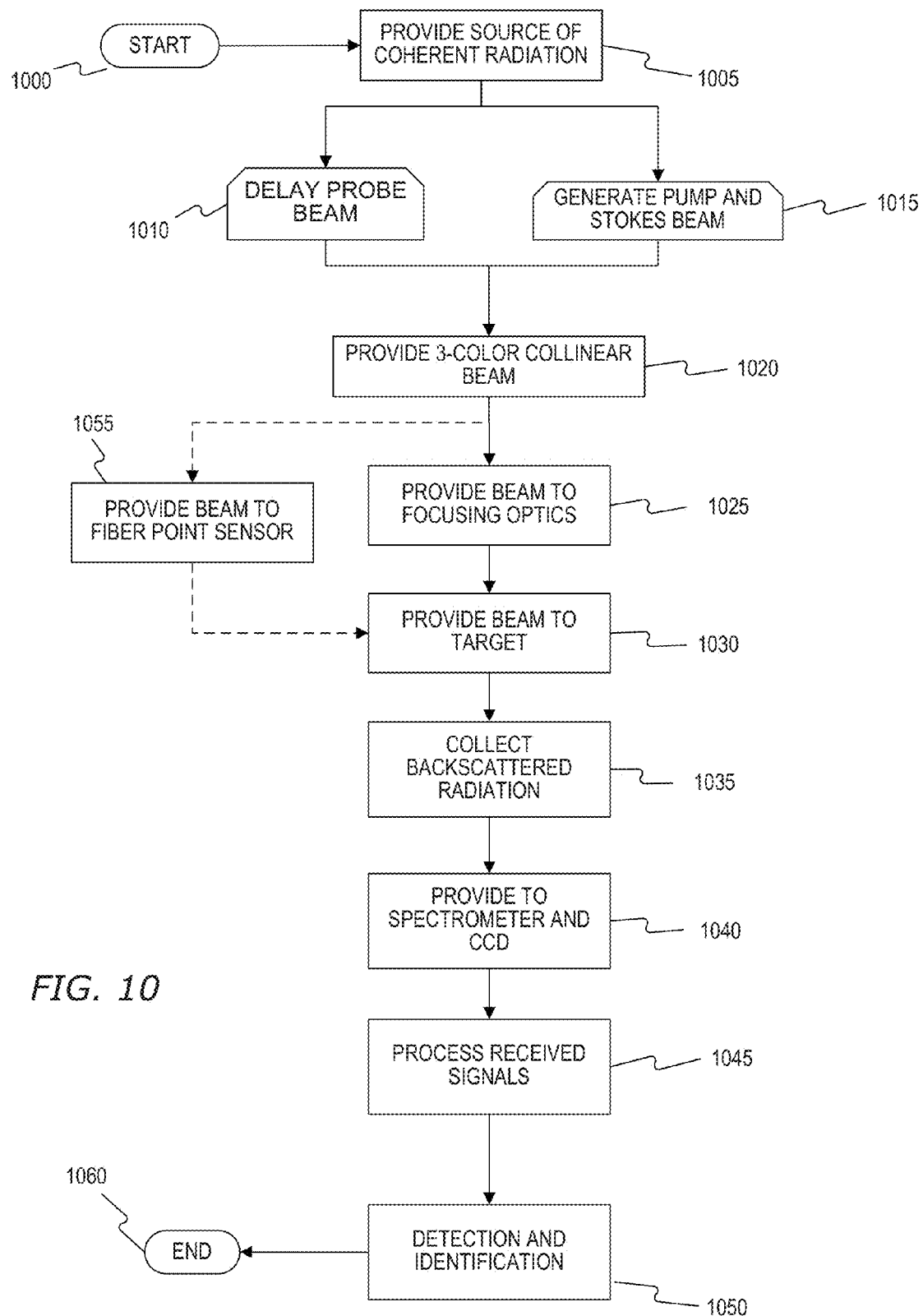
FIG. 10 depicts a flow-chart of a method consistent with the current disclosure.

FIG. 10 depicts an exemplary method of obtaining a CARS spectra consistent with the current disclosure. Step 1005 can include providing a source of coherent radiation. This can include providing a commercial amplified laser system, such as system 305, which can provide approximately 100 fs pulses at a frequency of approximately 1 kHz. Alternatively, or in addition, step 1005 can include providing laser system 705, which can be configured to generate a beam for inputting to a photonic crystal fiber, where the laser system 705 is configured to provide variable power to the generated laser pulses. Consistent with this disclosure, step 1010 can include delaying a probe beam generated by the source of coherent radiation. In addition, step 1015 can include generating a pump beam and a stokes beam. In connection with the system of FIGS. 3 and 4, a generated pump beam can correspond to a signal beam from OPA 320, and a generated Stokes beam can correspond to an idler beam from OPA 320. Alternatively, or in addition, step 1015 can include configuring the PCF 710, a circulator, and the FBG 825 in order to isolate a pump beam 892 and a Stokes beam 893 (in connection with the system of FIGS. 8 and 9).

Step 1020 can include combining the three-color beams generated (and or isolated) in steps 1010 and 1015 into a collinear beam. In connection with the system of FIGS. 3 and 4, this can include configuring the system as shown prior to the use of lens 340 and/or lens 440. In connection with the system of FIGS. 8 and 9, this can include the use of the splitter/combiner 840.

Steps 1025, 1030, 1035 can include, respectively, providing the beam to focusing optics, providing the beam to a target, and collecting backscattered radiation. Steps 1025, 1030, and 1035 allow for standoff operation. The focusing optics of step 1025 can include a lens or telescope. In a preferred embodiment, and in order to generate a line-configured target, the focusing optics can include a cylindrical lens, or a comparable optical device that allows for the generation of a focused line including the three-color collinear beam. Step 1030 then includes providing the beam to a target.

Alternatively to providing the beam to focusing optics, the beam can be provided to a fiber-based proximity sensor as indicated in step 1055. Under either step 1025 or step 1055, the beam can then be provided to a target (step 1030). Moreover, the backscattered radiation can be collected (step 1035) as depicted in FIG. 3, 4, or 9. Where a fiber-based proximity sensor is used and provides the beam to the target through a fiber, the backscattered radiation can be collected by the same fiber provided to a spectrometer via the fiber.

Step 1045 can include the signal processing, which can further include (without limitation): (a) baseline correction; (b) spectral smoothing; (c) SNR estimation; (d) normalization; and (e) determining a detection threshold.

Further step 1050 can include detection and identification of materials in the target. Step 1050 can further include, without limitation: (a) threshold based detection of potential targets; (b) template matching of stored sample signature against acquired target signature; and (c) discriminating between targets with similar features.

Consistent with the disclosure, systems and methods described herein can be used to detect small traces of solids and liquids at standoff range using a combination of time-delayed, collinear laser pulses at select wavelengths. Systems and methods disclosed herein also provide for imaging detection using hyperspectral imaging. In certain embodiments, the disclosed systems and methods herein can include the generation of a line-configured target. Alternatively, or in addition, systems and methods disclosed herein can utilize photonic crystal fibers in order to create and use a portable fiber-based system. A portable, fiber-based system consistent with this disclosure can be used for proximity detection and classification, fingerprint scanning, fiber-probing of surfaces, etc.

In embodiments disclosed herein, the systems and methods can be used for: (1) standoff detection of liquid and solid traces; (2) chemical and/or biological agent identification from a distance; (3) identification of biological targets such as blood, skin, etc.; and (4) real-time monitoring of an environment (such as for trace species).

As disclosed herein a fiber-based proximity sensor 880 can include a fiber tip, and can be configured (without limitation) as a pen-like probe, and can consist of a tip of a fiber, or a combination of a fiber and lens or microscope objective. Such a fiber tip can be used to perform real-time chemical detection, molecular identification, and chemical imaging. Further still, a system utilizing the disclosed fiber-based proximity sensor can be made portable, can include a sensor that can be scanned over the surface of interest, and the system can identify traces of the targets of interest. Such targets can include explosive residues, drugs, or other materials of interest. In a hospital setting, systems and methods disclosed herein can be configured to monitor fluids (blood) in realtime, or spectroscopically examine skin of subjects. Such systems and methods can also be utilized endoscopically for diagnostic and monitoring purposes.

Additional embodiments can include using the systems and methods disclosed herein for fast scanning of surfaces, and providing fingerprint scanning for traces of substances of interest (explosives, drugs, etc.).

Other embodiments will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for remote detection, the system comprising:
   a source of coherent laser pulses;
   a parametric amplifier configured to convert the coherent laser pulses into first beam pulses at a first wavelength value and second beam pulses at a second wavelength value different from the first wavelength value;
   a first optical component configured to select third beam pulses from the coherent laser pulses at a third wavelength value different from the second wavelength value and the first wavelength value;
   a second optical component configured to delay at least one of the first beam pulses, the second beam pulses, and the third beam pulses in order to create delayed beam pulses; and
   a focusing component configured direct a substantially collinear combination of the delayed beam pulses and two of a set of: the first beam pulses, the second beam pulses, and the third beam pulses, onto a line, the line being substantially perpendicular to a direction of propagation of the collinear combination.

2. The system of claim 1, wherein the at least one of the first beam pulses, the second beam pulses and the third beam pulses are the third beam pulses, and wherein the first beam pulses are pump beam pulses, the second beam pulses are Stokes beam pulses, and the third beam pulses are probe beam pulses.

3. The system of claim 1, wherein the first optical component is a filter.

4. The system of claim 1, wherein the second optical component comprises a system configured to add a variable path in free-space.

5. The system of claim 1, further comprising an imaging system configured to project a backscattered signal from the line onto an imaging spectrometer as a second line, the imaging spectrometer configured to disperse the second line to generate an image, the generated image being acquired by a CCD camera.

6. A method for remote detection, the method comprising:
   providing a source of coherent laser pulses;
   converting the coherent laser pulses into first beam pulses at a first wavelength value and second beam pulses at a second wavelength value different from the first wavelength value;
   selecting third beam pulses from the coherent laser pulses at a third wavelength value different from the second wavelength value and the first wavelength value;
   delaying at least one of the first beam pulses, the second beam pulses, and the third beam pulses in order to create delayed beam pulses; and
   directing a substantially collinear combination of the delayed beam pulses and two of a set of: the first beam pulses, the second beam pulses, and the third beam pulses, onto a line, the line being substantially perpendicular to a direction of propagation of the collinear combination.

7. The method of claim 6, wherein the at least one of the first beam pulses, the second beam pulses and the third beam pulses are the third beam pulses, and wherein the first beam pulses are pump beam pulses, the second beam pulses are Stokes beam pulses, and the third beam pulses are probe beam pulses.

8. The method of claim 6, wherein selecting third beam pulses uses a narrow bandpass filter.

9. The method of claim 6, wherein delaying includes addition of variable path in free-space.

10. The method of claim 6, further comprising projecting a backscattered signal from the line onto an imaging spectrometer as a second line, the imaging spectrometer configured to disperse the second line to generate an image, the generated image being acquired by a CCD camera.

11. A portable detection system, the system comprising:
    a source of coherent laser pulses, wherein the source is configured to provide the laser pulses at a plurality of power values, and wherein the coherent laser pulses are configured to exhibit a first spectral distribution as a function of the plurality of power values;
    a length of photonic crystal fiber configured to generate coherent, converted pulses from the coherent laser pulses, wherein the coherent, converted pulses exhibit a second spectral distribution as a function of the plurality of power values, wherein the second spectral distribution is different from the first spectral distribution at at least one power value of the plurality of power values;
    a first optical system configured to select first beam pulses at a first wavelength value and second beam pulses at a second wavelength value different from the first wavelength value from the coherent, converted pulses;
    a second optical system configured to select third beam pulses from the coherent, converted pulses at a third wavelength value different from the second wavelength value and the first wavelength value; and
    a third optical component configured to delay at least one of the first beam pulses, the second beam pulses, and the third beam pulses in order to create delayed beam pulses.

12. The system of claim 11, further comprising a proximity sensor component configured to direct a substantially collinear combination of the delayed beam pulses and two of a set of: the first beam pulses, the second beam pulses, and the third beam pulses onto a sample.

13. The system of claim 12, further comprising a spectrometer, wherein the proximity sensor comprises a fiber, and wherein the spectrometer is configured to acquire a backscattered signal from the sample through the fiber.

14. The system of claim 12, wherein the proximity sensor comprises a flexible fiber, and wherein the flexible fiber is configured to be manipulated proximal to the sample.

15. The system of claim 11, wherein the first optical system comprises a fiber Bragg grating and a circulator.

16. The system of claim 15, wherein the second optical component comprises the circulator.

17. The system of claim 11, further comprising:
    a focusing component; and
    and imaging system;
    wherein the focusing component is configured to direct a substantially collinear combination of the delayed beam pulses and two of a set of: the first beam pulses, the second beam pulses, and the third beam pulses onto a sample; and
    wherein the imaging system is configured to project a backscattered signal from the sample onto an imaging spectrometer, the imaging spectrometer configured to generate an image, the generated image being acquired by a CCD camera.

18. The system of claim 17, wherein the focusing component is further configured to scan over the sample.

19. The system f claim 11, further comprising an imaging system configured to project a backscattered signal from the sample onto an imaging spectrometer, the imaging spectrometer configured to generate an image, the generated image being acquired by a CCD camera.

20. A method for portable detection, the method comprising:
providing a source of coherent laser pulses, wherein the source is configured to provide the laser pulses at a plurality of power values, and wherein the coherent laser pulses are configured to exhibit a first spectral distribution as a function of the plurality of power values;
providing a length of photonic crystal fiber configured to generate coherent, converted pulses from the coherent laser pulses, wherein the coherent, converted pulses exhibit a second spectral distribution as a function of the plurality of power values, wherein the second spectral distribution is different from the first spectral distribution at at least one power value of the plurality of power values;
selecting first beam pulses at a first wavelength value and second beam pulses at a second wavelength value different from the first wavelength value from the coherent, converted pulses;
selecting third beam pulses from the coherent, converted pulses at a third wavelength value different from the second wavelength value and the first wavelength value;
delaying at least one of the first beam pulses, the second beam pulses, and the third beam pulses in order to create delayed beam pulses; and
directing a substantially collinear combination of the delayed beam pulses and two of a set of: the first beam pulses, the second beam pulses, and the third beam pulses onto a sample.

21. The method of claim 20, wherein the step of directing uses a proximity sensor component.

22. The method of claim 21, wherein the proximity sensor comprises a fiber, and wherein a spectrometer is configured to acquire a backscattered signal from the sample through the fiber.

23. The method of claim 21, wherein the proximity sensor comprises a flexible fiber, and wherein the flexible fiber is configured to be manipulated proximal to the sample.

24. The method of claim 20, wherein selecting first beam pulses at the first wavelength value and second beam pulses at the second wavelength value different from the first wavelength value uses a fiber Bragg grating and a circulator.

25. The method of claim 24, wherein selecting third beam pulses uses the circulator.

26. The method of claim 20, further comprising:
directing a substantially collinear combination of the delayed beam pulses and two of a set of: the first beam pulses, the second beam pulses, and the third beam pulses onto a sample; and
projecting a backscattered signal from the sample onto an imaging spectrometer, the imaging spectrometer configured to generate an image, the generated image being acquired by a CCD camera.

27. The method of claim 26, wherein directing a substantially collinear combination includes scanning the collinear combination over the sample.

28. The method of claim 20, further comprising projecting a backscattered signal from the sample onto an imaging spectrometer, the imaging spectrometer configured to generate an image, the generated image being acquired by a CCD camera.

* * * * *